United States Patent [19]
Yamanashi et al.

[11] Patent Number: 6,059,781
[45] Date of Patent: May 9, 2000

[54] ELECTROCONVERGENT CAUTERY SYSTEM

[76] Inventors: William S. Yamanashi, 2018 E. 73rd St., Tulsa, Okla. 74136; Arun Angelo Patil, 6105 Chicago St., Omaha, Nebr. 68132

[21] Appl. No.: 08/101,228

[22] Filed: Aug. 3, 1993

Related U.S. Application Data

[63] Continuation-in-part of application No. 07/967,685, Oct. 27, 1992, abandoned.

[51] Int. Cl.7 .................................................. A61B 17/36
[52] U.S. Cl. ............................................... 606/45; 606/49
[58] Field of Search ................................ 606/32–35, 37, 606/38, 41–45, 49, 52

[56] References Cited

U.S. PATENT DOCUMENTS

| | | | |
|---|---|---|---|
| 3,938,527 | 2/1976 | Rioux et al. | 128/303.17 |
| 3,963,030 | 6/1976 | Newton | 606/38 |
| 4,041,952 | 8/1977 | Morrison, Jr. et al. | 128/303.13 |
| 4,092,986 | 6/1978 | Schneiderman | 606/38 |
| 4,353,371 | 10/1982 | Cosman | 128/303.17 |
| 4,517,975 | 5/1985 | Garito et al. | 128/303.13 |
| 5,011,483 | 4/1991 | Sleister | 606/37 |
| 5,019,076 | 5/1991 | Yamanashi et al. | 606/45 |
| 5,116,333 | 5/1992 | Beane | 606/51 |

*Primary Examiner*—Michael Peffley
*Attorney, Agent, or Firm*—Zarley, McKee, Thomte Voorhees & Sease; Dennis L. Thomte

[57] ABSTRACT

A surgical tool for surgically treating tissue in a patient comprising a radio frequency power generator for creating an alternating current having an impedance matching circuit connected thereto for matching the impedance of a surgical instrument with the radio frequency generator. A loading and tuning coil is connected to a watts/ampere meter which is connected to the impedance matching circuit. The loading and tuning coil is connected to a surgical instrument which has a tip for focusing the radio frequency current at the region of the tissue such that the tissue being contacted is instantaneously vaporized and cut and/or cauterized.

13 Claims, 3 Drawing Sheets

ELECTROCONVERGENT CAUTERY SYSTEM

CROSS REFERENCE TO RELATED APPLICATION

This is a continuation-in-part application of Ser. No. 967,685 entitled "AN ELECTROCONVERGENT CAUTERY SYSTEM," filed Oct. 27, 1992, now abandoned.

BACKGROUND OF THE INVENTION

1. Field of the Invention

This invention relates to an electroconvergent cautery system employing forceps or probes which produce sharply localized heating for cutting, vaporizing tissue and coagulating blood vessels when brought into contact with the same.

2. Description of the prior art

Monopolar cautery systems have been in use for the last seventy to eighty years. Monopolar electrocautery systems are used for coagulating vessels and for cutting tissue. In the prior electrocautery systems, high frequency electric current is passed from the cautery probe through the tissue to the grounding pad. Heat is generated in the tissue at the site of contact of the probe tip to the tissue by the flow of current through the electrical resistance of the tissue in the preferred path between the probe tip contact site and the grounding pad. In such devices, the current is continuous sinusoidal or amplitude modulated. The heat generated by the cautery of the prior monopolar electrocautery systems is not uniform since the heating of the tissue is greater in the preferred path of current of lower resistance. For this reason, as the current flows from the point of contact of the probe to the surrounding tissue, heating also tends to spread beyond the contact point of the probe to the surrounding tissue thereby causing damage to the surrounding tissue. The problems associated with the prior monopolar electrocautery systems were overcome by the bipolar cautery system, which causes current to flow from one tip of the forceps to the other tip of the forceps without the spread of current to the surrounding tissues. Both the monopolar electrocautery and the bipolar cautery system can cut tissue and coagulate vessels but cannot vaporize tissue.

Radio frequency (RF) lesion generators work on the same principle as the monopolar cautery system except that a lower level of current is used and the current is of the continuoussinusoidal type resulting in more uniform tissue destruction. However, such a system is used exclusively for creating lesions.

In an effort to resolve the problems of the prior art, the inventors invented a radio frequency surgical tool which is disclosed in U.S. Pat. No. 5,019,076. The tool of U.S. Pat. No. 5,019,076 is capable of cutting and vaporizing tissue and coagulating vessels without the spread of heat to the surrounding tissue. In the device of said patent, a high frequency (13.56 or 27.0 MHz) current is passed through an amplifier, a matching network and a solenoid coil to generate an electromagnetic field. This in turn induces eddy currents in the tissue. Touching the tissue by a probe which is AC-coupled to a return circuit draws the eddy currents out of the tissue at the contact point of the probe producing intense heat which can cut and vaporize tissue as well as coagulate vessels. One disadvantage of the system of the said patent is the proximity of the coil in the operative field causing inconvenience to the surgeon. A further disadvantage of the device of said patent is that the coagulating ability of the device is not as efficient as desired.

SUMMARY OF THE INVENTION

An electroconvergent cautery system is described which is used as a surgical tool for coagulating blood vessels and cutting and vaporizing tissue. Electrical current is passed through either a surgical probe or forceps. The current is generated by a radio frequency power generator which produces an alternating current of 13.56 or 27.0 MHz. An optional variable crest factor setting unit pulse modulates the sinusoidal to a variable interval square pulse of approximately 30 Hz–30 KHz and varies duty cycle and pulse height. An impedance matching device is utilized to match the impedance of the probe or the active blade of the forceps with the radio frequency power generator. A loading tuning coil serves as an auto transformer which minimizes the mismatch of impedance of the probe or the active blade of the forceps with the radio frequency generator upon touching the tip of the probe or the active blade of the forceps to the tissue. This causes the current to converge to the tip and results in high current density at the tip of the probe or the active blade of the forceps. Furthermore, the loading and tuning coil instantaneously causes the current at the probe tip to capacitatively couple with the return circuit drawing back the current into the return circuit. The high current density at the sharp tip of the probe or the active blade of the forceps produces intense localized heating which is capable of coagulating vessels and cutting and vaporizing tissue. As the current is instantaneously drawn back into the return circuit, the heat is restricted to the contact point. When vessels are held between the two tips of the forceps some energy is dissipated into the inactive blade resulting in diffuse heating which improves its coagulating property. Furthermore, while holding vessels between the two blades of the forceps, the contact of tissue is slightly proximal to the tip of the blade. This results in increased area of contact between the forceps and the tissue resulting in less intense and more diffuse heating which improves its coagulating property. A similar effect can also be achieved with the probe, by touching the tissue with the probe slightly proximal to its tip.

In the surgical forceps configuration, the two blades of the forceps, except for their tips, are insulated. The two blades at their proximal ends are separated by heavily insulated material. One of the blades serves as an active blade and is connected to the loading and tuning coil by means of a heavily insulated cable. The other blade of the surgical forceps is a passive blade and has no electrical connection. The two blades taper towards their sharply pointed tips with the tip of the active blade being approximately 0.25 mm longer than that of the passive blade. Any shape or size of existing surgical forceps may be connected to the system.

An endoscopic and endovascular probe is also disclosed which consists of a ⅝, ⅜, or ½n wavelength long (wherein "n" is an integer) heavily insulated flexible or rigid wire with an exposed tip of required length. The distal end of the tip is sharply pointed with the tip being straight, curved or angled.

Also described is a laparoscopic probe having a probe similar to the endoscopic probe except that the probe is rigid and the tip is bent at a right angle. Further described is a surgical probe comprised of a rigid wire with a tapered fine tip. Except for the exposed tip, the remainder of the probe is insulated with a pencil shaped configuration.

It is therefore a principal object of the present invention to provide an electroconvergent cautery system which can coagulate blood vessels and cut and vaporize tissue without the spread of heat to the surrounding tissue.

Yet another object of the invention is to provide an electroconvergent cautery system which eliminates the need of a coil in the operative field.

Yet another object of the invention is to provide an electroconvergent cautery system utilizing surgical forceps having a pair of blades with one of the blades being a passive blade and the other blade being an active blade.

Still another object of the invention is to provide an electroconvergent cautery system including surgical forceps with the two blades thereof tapering towards their sharply pointed tips with the tip of the active blade being approximately 0.25 mm longer than that of the passive blade so that the tip of the former will touch tissue to cut and vaporize it without being obstructed from the surgeon's vision by the latter.

Yet another object of the invention is to provide an electroconvergent cautery system with any size or shape of surgical forceps.

Still another object of the invention is to provide an electroconvergent cautery system including laparoscopic forceps wherein the blades are short and the main stems thereof are long.

Still another object of the invention is to provide an electroconvergent cautery system including an endoscopic and endovascular probe with the probe consisting of a heavily insulated flexible or rigid wire having an exposed tip of approximately 5 mm with the distal end of the tip being sharply pointed with the tip either being straight, curved or angled.

Yet another object of the invention is to provide an electroconvergent cautery system including a laparoscopic probe the probe thereof being rigid and the tip being bent at a right angle.

Still another object of the invention is to provide an electroconvergent cautery system including a surgical probe comprised of a rigid wire with a tapered fine tip.

Still another object of the invention is to provide an electroconvergent cautery system including a lesion generating probe for ablation of various accessory pathways in the heart for arythmic patients.

These and other objects of the present invention will be apparent to those skilled in the art.

DESCRIPTION OF THE PREFERRED EMBODIMENT

Figure 1:
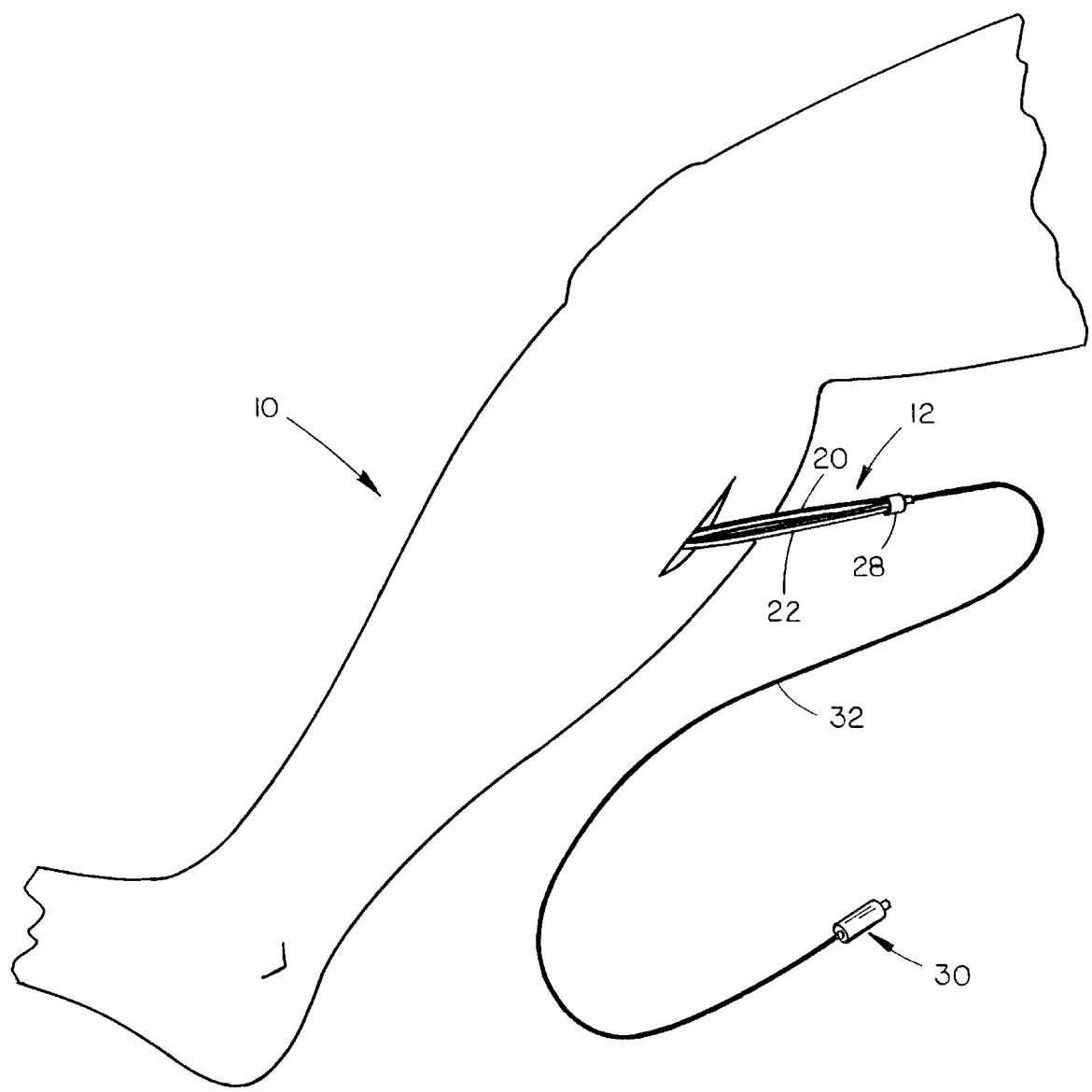
FIG. 1 is a perspective view of and form of an instrument utilized in the electroconvergent cautery system of this invention.

Referring to the drawings, the numeral 10 designates a human leg while the numeral 12 refers to a cautery instrument in the form of surgical forceps. A variety of cautery instruments are interchangeable in the electroconvergent cautery system such as the surgical forceps 14 in FIG. 3, laparoscopic forceps 16 in FIG. 4 and the surgical probe 18 illustrated in FIG. 5.

Figure 2:
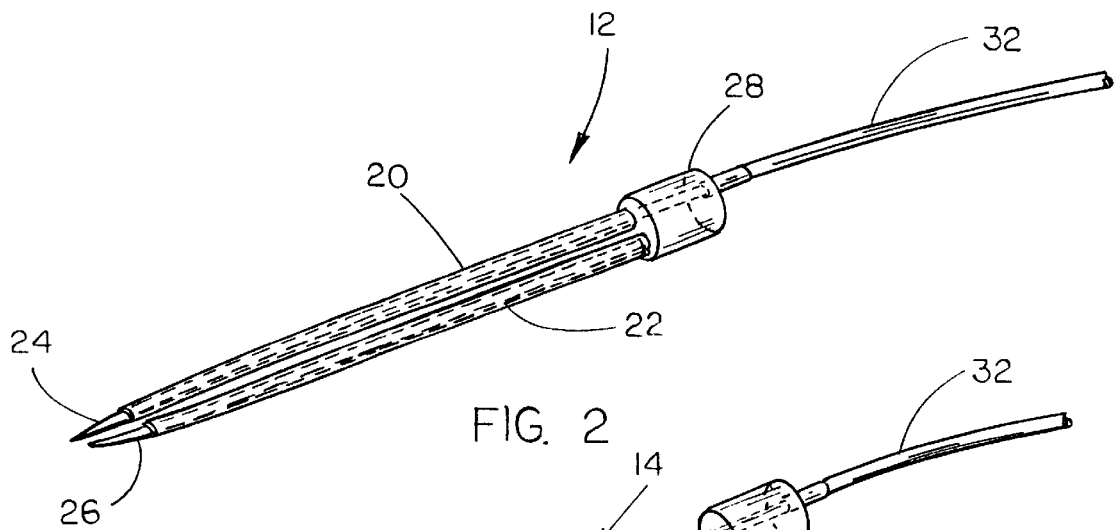
FIG. 2 is a perspective view of straight surgical forceps connected to an electric cable for use as an electroconvergent cautery instrument.

The surgical forceps 12 illustrated in FIG. 2 comprises a pair of straight blades 20 and 22 which are insulated except for the tips 24 and 26. Blades 20 and 22 are separated at their proximal ends by a heavily insulated material referred to generally by the reference numeral 28. Blade 20 serves as the active blade and is connected to the loading and tuning coil 30 by means of a heavily insulated cable 32. Blade 22 is passive and has no electrical connections. As seen in FIG. 2, blades 20 and 22 taper towards their sharply pointed tips. Tip 24 of blade 20 is approximately 0.25 mm longer than the tip of the passive blade 22.

Figure 3:
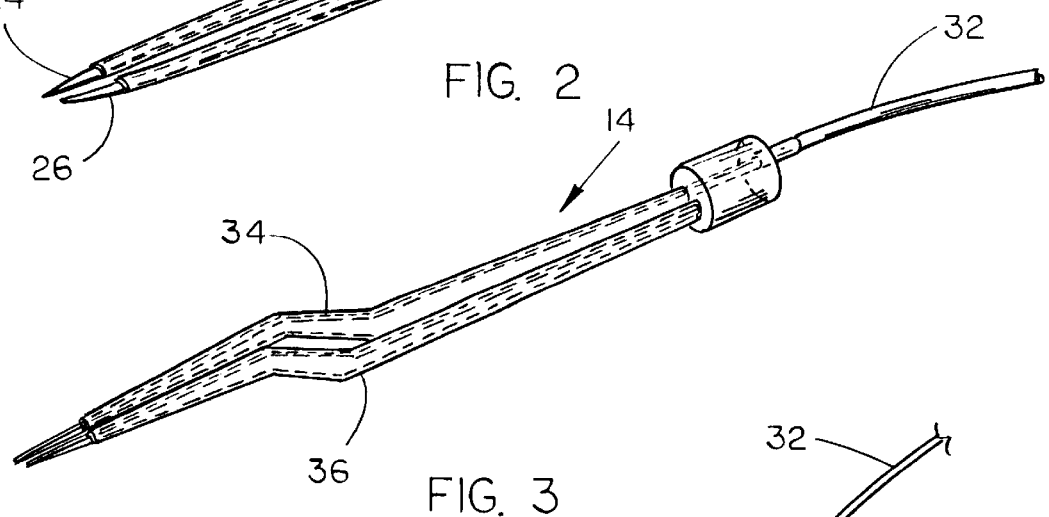
FIG. 3 is a view similar to FIG. 2 except that the forceps are bayonetted.

With respect to FIG. 3, the surgical forceps 14 illustrated therein are generally similar to the forceps shown in FIG. 2 except that the blades 34 and 36 are bayonetted. Blade 34 is the active blade and is electrically connected to the insulated cable 32. As in the surgical forceps 12, the tips of the active blade 34 is approximately 0.25 mm longer than that of the tip of the blade 36.

Figure 4:
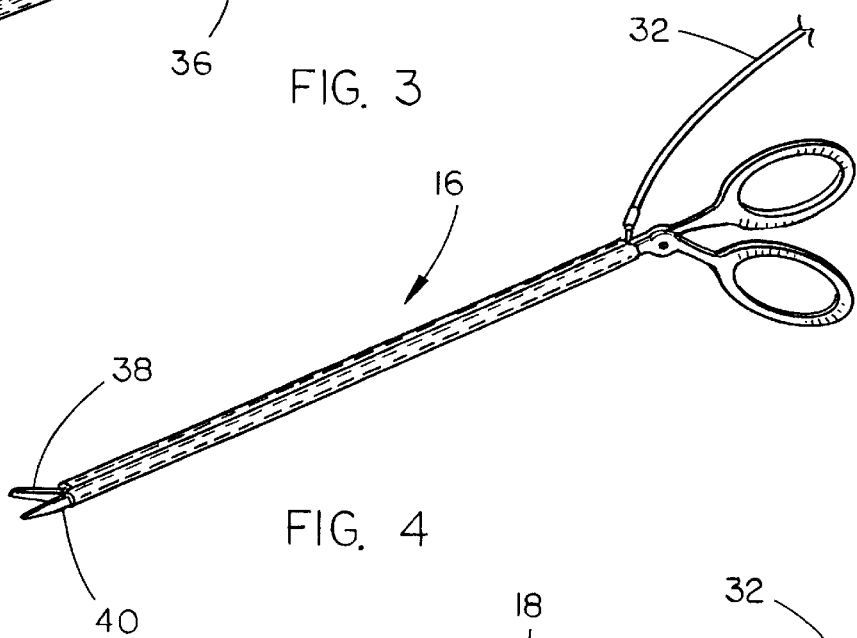
FIG. 4 is a perspective view of laparoscopic forceps similar to that shown in FIGS. 2 and 3 except that the blades are short and the main stems are long.

FIG. 4 illustrates a laparoscopic forceps which is similar to the surgical forceps of FIGS. 2 and 3 above except that the blades 38 and 40 are short with the main stems thereof being quite long. Blade 38 is operatively connected to the insulated cable 32.

Figure 5:
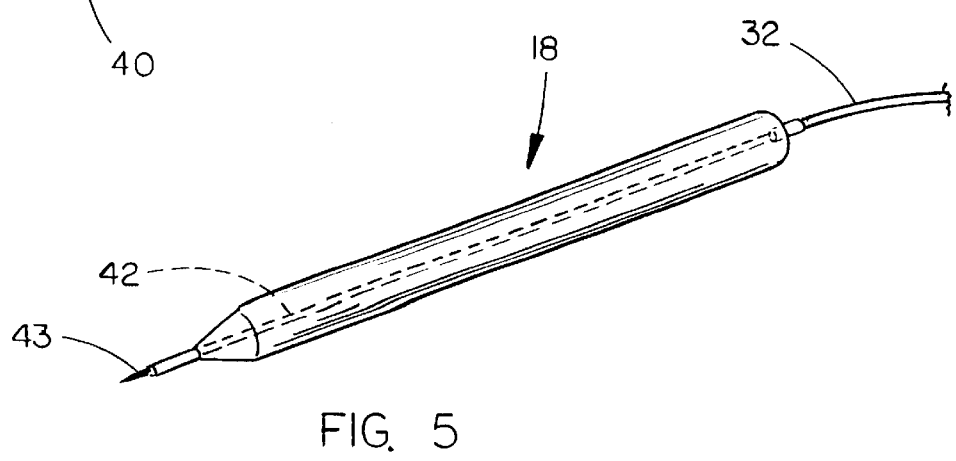
FIG. 5 is a perspective view of a surgical probe which may be used with the system of this invention.

The surgical probe 18 illustrated in FIG. 5 comprises a rigid wire 42 with a tapered fine tip 43. Except for approximately 5 mm of the tip 43, the remainder of the probe is insulated in pencil shaped configuration for gripping purposes.

An endoscopic probe may also be provided which is generally similar to the surgical probe 18 of FIG. 5 except that the tip portion thereof may be straight, curved or angled. The outer diameter of the probe would be approximately 0.75 to 2 mm. The length of the probe would be a multiple of 22 and may be rigid or flexible. This probe may be used as a resectoscope or as an endovascular probe. Further, the probe could have its tip bent at a right angle.

Figure 7:
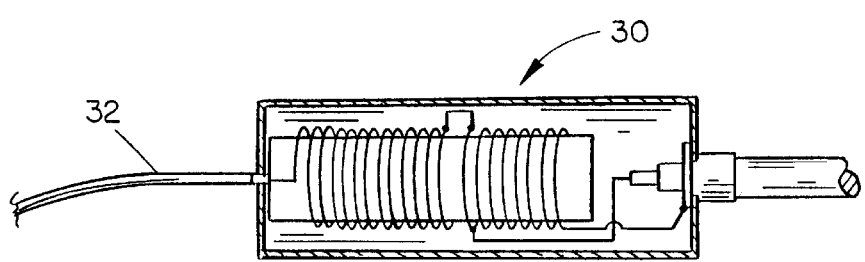
FIG. 7 is a sectional view of the loading and tuning coil of this invention.
Figure 6:
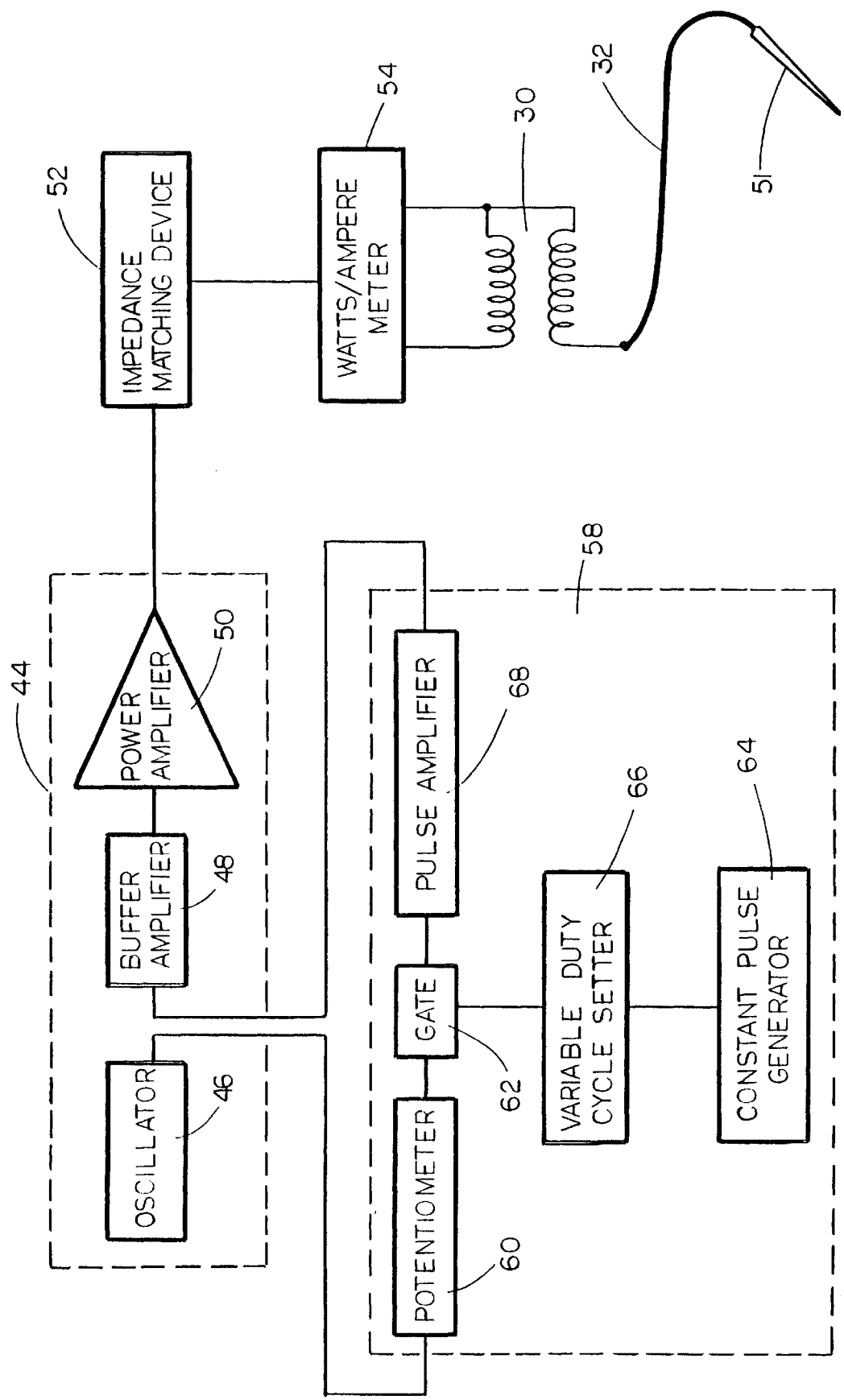
FIG. 6 is a schematic of the electrical circuitry of the system.

The cautery instruments of FIGS. 2, 3, 4 and 5 are to be utilized with electrical circuitry illustrated in FIG. 6 and 7. Inasmuch as many of the components of that shown in FIG. 6 are identical or similar to that taught in U.S. Pat. No. 5,019,076, reliance upon said patent is made to complete this disclosure, if necessary. In other words, the parameters or specifications of the various components of FIG. 6 will not be described since it is believed that the same are disclosed in U.S. Pat. No. 5,019,076 or would be obvious to one having ordinary skill in the art.

The numeral 44 refers to a radio frequency power generator comprises an oscillator 46, buffer amplifier 48 and power amplifier 50. As seen in FIG. 6, an impedance matching device 52 is electrically connected to the radio frequency power generator. A watts/ampere meter 54 is electrically connected to the impedance matching device 52 and is electrically connected to the loading and tuning coil 30. Loading and tuning coil 30 is connected to the surgical instrument SI by means of the heavily insulated cable 32. As stated, the surgical instrument SI may be comprised of those instruments previously described. The cable 32 connects the surgical instrument SI to the loading and tuning coil 30 as described and would have a length of 110 centimeters or a multiple of 22.

A variable crest factor setting unit 58 is interposed between the oscillator 46 and the buffer amplifier 48. Variable crest setting factor 58 is comprised of a peak voltage setting potentiometer 60, a gate 62, a constant pulse generator 64, a variable duty cycle setter 66 and a pulse amplifier 68.

The RF power generator 44 generates an alternating current of 13.56 or 27 MHz. The variable crest factor setting unit 66 modulates the waveform to a continuous wave with square wave of approximately 30 Hz–30 KHz and varies duty cycle and pulse height. The impedance matching device 52 matches the impedance of the probe or forceps with the RF generator 44. The loading and tuning coil 30 together serves as an autotransformer. When the probe tip touches the tissue, the mismatch of impedance between the probe and the radio frequency generator is nullified resulting in high current density at the tip of the probe or the active blade of the forceps which in turn results in high temperature at the contact point. Furthermore, the loading and tuning coil causes the current at the probe tip to capacitively couple with the return circuit. Therefore, touching the sharp tip of the probe or the active blade of the forceps to the tissue produces sharply localized heating which can cut and vaporize tissue. When vaporizing or cutting tissue, the active blade touches the tissue due to its longer length. Furthermore, when the vessels are held between the two tips of the forceps, the contacted tissue is slightly proximal to the tip. Such results in an increased area of contact between the forceps and the tissue resulting in less intense and more diffuse heating which is ideal for coagulation. A similar effect can also be achieved by touching the tissue with the probe slightly proximal to its tip.

Thus, it can be seen that the invention accomplishes at least all of the stated objectives.

We claim:

1. A surgical tool for surgically treating tissue in a patient, comprising:

a radio frequency power generator for creating an alternating current of a pre-selected frequency;

said radio frequency generator including an oscillator, a buffer amplifier and a power amplifier;

said buffer amplifier and said power amplifier being series connected;

an impedance matching means connected to said power amplifier for matching the impedance of a probe with the radio frequency generator;

a watts/ampere meter connected to said impedance matching means;

a loading and tuning coil connected to said watts/ampere meter;

a probe for contact with the tissue;

said loading and tuning coil being connected to said probe, said probe having a tip means for transmitting, receiving and focusing the radio frequency current at the region of the tissue such that the tissue being contacted is instantaneously vaporized, cut and/or cauterized.

2. The surgical tool of claim 1 wherein said probe has a pencil configuration.

3. The surgical tool of claim 1 wherein said probe has the configuration of one blade of a forceps.

4. The surgical tool of claim 1 wherein said probe is a rigid wire.

5. The surgical tool of claim 1 wherein said probe is a flexible wire.

6. The surgical tool of claim 1 wherein said probe is a knife.

7. The surgical tool of claim 1 wherein said probe is a straight tip.

8. The surgical tool of claim 1 wherein said probe is a curved tip.

9. The surgical tool of claim 1 wherein said probe is an angular tip.

10. A surgical tool of claim 1 wherein a variable crest factor setting unit interconnects said oscillator and said buffer amplifier for modulating the waveform created by said radio frequency power generator to a continuous square wave and for varying the duty cycle and pulse height of the waveform.

11. A surgical tool for treating tissue comprising the combination of:

(a) a radio frequency source means for creating an alternating current for a preselected frequency, waveform and duty cycle;

(b) an electrically conductive and insulated metal probe including an exposed and uninsulated tip means for contact with the region of the tissue to be treated;

(c) An impedance matching means interconnecting said probe with said radio frequency source;

(d) a loading and tuning coil means imposed between said impedance matching device and said probe and being located remote from said probe and the tissue to be treated;

(e) said loading and tuning coil functioning as an autotransformer whereby when said tip means contacts the tissue to be treated, the mismatch between the radio frequency generator and the tip means is nullified resulting in a high bolus at said tip means; and (f) said loading and tuning coil causing the current at said tip means to capacitatively couple with the return circuit from said tip means thereby drawing the current back into the return circuit.

12. The combination of claim 11 wherein said metal probe compromises a forceps having an active blade electrically connected to said loading and tuning coil and an inactive blade.

13. The combination of claim 11 wherein said active blade is slightly longer than said inactive blade so that during its use it is visible to the surgeon.

* * * * *